(12) United States Patent
Lee et al.

(10) Patent No.: US 10,464,867 B2
(45) Date of Patent: Nov. 5, 2019

(54) DISTILLATION METHOD

(71) Applicant: LG CHEM, LTD., Seoul (KR)

(72) Inventors: Sung Kyu Lee, Daejeon (KR); Ho Joon Shin, Daejeon (KR)

(73) Assignee: LG CHEM, LTD., Seoul (KR)

( * ) Notice: Subject to any disclaimer, the term of this patent is extended or adjusted under 35 U.S.C. 154(b) by 118 days.

(21) Appl. No.: 15/510,134

(22) PCT Filed: Nov. 2, 2015

(86) PCT No.: PCT/KR2015/011654
§ 371 (c)(1),
(2) Date: Mar. 9, 2017

(87) PCT Pub. No.: WO2016/068677
PCT Pub. Date: May 6, 2016

(65) Prior Publication Data
US 2017/0320796 A1   Nov. 9, 2017

(30) Foreign Application Priority Data

Oct. 31, 2014 (KR) .................. 10-2014-0150672
Nov. 2, 2015  (KR) .................. 10-2015-0153088

(51) Int. Cl.
| C07C 7/04 | (2006.01) |
| B01D 3/14 | (2006.01) |
| C07C 11/02 | (2006.01) |
| B01D 3/00 | (2006.01) |
| C07C 9/15 | (2006.01) |
| B01D 3/32 | (2006.01) |
| B01D 3/42 | (2006.01) |

(52) U.S. Cl.
CPC ............... *C07C 7/04* (2013.01); *B01D 3/007* (2013.01); *B01D 3/143* (2013.01); *B01D 3/32* (2013.01); *B01D 3/42* (2013.01); *B01D 3/4211* (2013.01); *C07C 9/15* (2013.01); *C07C 11/02* (2013.01)

(58) Field of Classification Search
CPC ......... B01D 3/007; B01D 3/143; B01D 3/32; B01D 3/42; B01D 3/4211; C07C 7/04; C07C 9/15; C07C 11/02
See application file for complete search history.

(56) References Cited

U.S. PATENT DOCUMENTS

| 4,177,111 A | 12/1979 | Pieper et al. |
| 4,555,311 A * | 11/1985 | Ward ..................... B01D 3/143 203/21 |

(Continued)

FOREIGN PATENT DOCUMENTS

| CA | 2387169 A1 * | 11/2003 | ............... B01D 3/40 |
| CN | 103396305 A | 11/2013 | |

(Continued)

*Primary Examiner* — Youngsul Jeong
*Assistant Examiner* — Gabriel E Gitman
(74) *Attorney, Agent, or Firm* — Dentons US LLP (57) ABSTRACT

The present application relates to a distillation device. The distillation device of the present application can minimize energy loss occurring in a purification process of the olefin monomer, the solvent, and the raw material including, for example, 1-octene, iso-octene, and n-hexane, used in a polymerization process of the polyolefin elastomer, and can increase economic efficiency by isolating a high-purity product.

11 Claims, 1 Drawing Sheet

(56) References Cited

U.S. PATENT DOCUMENTS

| | | | | |
|---|---|---|---|---|
| 4,747,914 A | * | 5/1988 | Schwarzmaier | C07C 17/38 |
| | | | | 203/22 |
| 5,085,740 A | | 2/1992 | Lee et al. | |
| 5,435,436 A | | 7/1995 | Manley et al. | |
| 5,458,739 A | * | 10/1995 | Boucher | B01D 1/02 |
| | | | | 202/153 |
| 8,431,762 B2 | * | 4/2013 | Park | B01D 3/143 |
| | | | | 585/802 |

FOREIGN PATENT DOCUMENTS

| | | |
|---|---|---|
| JP | 61-90703 A | 5/1986 |
| JP | 05-305201 A | 11/1993 |
| KR | 10-1995-0011388 A | 5/1995 |
| KR | 10-2007-0025556 A | 3/2007 |
| KR | 10-2014-0092783 A | 7/2014 |
| KR | 10-2014-0092785 A | 7/2014 |
| KR | 10-2014-0098138 A | 8/2014 |
| WO | 99/065582 A1 | 12/1999 |
| WO | 2012/026955 A1 | 3/2012 |

* cited by examiner

DISTILLATION METHOD

The present application is a National Stage Application No. PCT/KR2015/011654, filed Nov. 2, 2015, and claims the benefit of priority based on Korean Patent Application No. 10-2014-0150672 dated Oct. 31, 2014 and Korean Patent Application No. 10-2015-0153088 dated Nov. 2, 2015, all of which are hereby incorporated by reference in their entirety for all purposes as if fully set forth herein.

TECHNICAL FIELD

The present application relates to a distillation device for isolating and collecting a solvent and an unreacted monomer used in a polymerization process of a polyolefin elastomer.

BACKGROUND ART

Polyolefin elastomers are used as materials having reinforcing properties, such as impact strength and flexural strength, of interior/exterior materials of automobiles. Additionally, polyolefin elastomers are used in various industries, such as the high-tech textiles industry and the sports industry, due to their superior elasticity, toughness, etc.

For example, polyolefin elastomers are polymerized according to a solution polymerization method wherein an olefin monomer is dissolved in a solvent and then polymerization is carried out using a catalyst, and a solvent is collected from a resultant polymerized solution, after which it is subjected to a drying process and packaged. When a polyolefin elastomer is prepared according to such a solution polymerization method, a large amount of solvent is used with respect to the amount of an added olefin monomer, and thus a large amount of energy is consumed in a process of collecting the solvent and an unreacted monomer after polymerization. Conventionally, a solvent and an unreacted monomer were collected from a polymerized solution including the solvent and the unreacted monomer after solution polymerization by means of a distillation device composed of two sequentially connected distillation columns. However, in this process, a large amount of energy is disadvantageously consumed.

Therefore, there is a need for a process of collecting a solvent and an unreacted monomer to reduce distillation device installation costs and isolate a high-purity compound.

DISCLOSURE

Technical Problem

The present application is directed to providing a distillation device for isolating and collecting a solvent and an unreacted monomer used in a polymerization process of a polyolefin elastomer with high purity and efficiency.

Technical Solution

One aspect of the present application provides a distillation device. A distillation device according to exemplary embodiments of the present application may increase economic efficiency of a process by minimizing energy loss occurring in a purification process of an olefin monomer, a solvent, and a raw material including, for example, 1-octene, iso-octene, and n-hexane used in the polymerization process of the polyolefin elastomer and isolating a product in high purity. In particular, the distillation device of the present application provides optimized temperature and pressure for isolating 1-octene, iso-octene, and n-hexane using two distillation units, thus isolating the solvent and the unreacted olefin monomer used in the polyolefin elastomer polymerization process with high purity and efficiency by means of the distillation device of the present application.

Hereinafter, the distillation device of the present application will be described with reference to the accompanying drawing. The drawing is, however, provided as an exemplary embodiment and the distillation device should not be understood as limited to the accompanying drawing.

The FIGURE exemplarily illustrates a distillation device according to an embodiment of the present application. As illustrated in the FIGURE, the distillation device according to an exemplary embodiment includes two distillation units 10 and 20 and a heat exchanger 30. For example, the distillation device includes the first and second distillation units 10 and 20 and the heat exchanger 30. The first distillation unit 10 includes a first distillation column 100, a first condenser 101, a storage tank 102, and a first reboiler 103. The second distillation unit 20 includes a second distillation column 200, a second condenser 201, a storage tank 202, and a second reboiler 203.

The first and second distillation columns 100 and 200 are devices for isolating various ingredients included in a raw material using boiling point differences thereamong. In the distillation device of the present application, distillation columns with various shapes may be used, considering ingredients of an introduced raw material or the boiling points of the ingredients to be separated. A distillation column type which may be used in the distillation device of the present application is not specifically limited and may be, for example, a distillation column with a general structure as illustrated in the FIGURE or a dividing wall-type distillation column including a dividing wall therein. In an example, the interiors of the first and second distillation columns 100 and 200 may be divided into upper sections 110 and 210, lower sections 130 and 230, and intermediate sections 120 and 220, as illustrated in the FIGURE. The expression "upper section," as used in the present specification, means a relatively upper portion of each of the first and second distillation columns 100 and 200. For example, when each of the first and second distillation columns 100 and 200 is divided into three parts in a height or length direction thereof, the upper section may be the uppermost section thereof. In addition, the expression "lower section" means a relatively lower portion of each of the first and second distillation columns 100 and 200. For example, when each of the first and second distillation columns 100 and 200 is divided into three parts in a height or length direction thereof, the lower section may be the lowest section thereof. In addition, when each of the first and second distillation columns 100 and 200 is divided into three parts in a height or length direction thereof, the expression "intermediate section" as used in the present specification may mean an intermediate section among the divided sections and a section between the upper section 110 or 210 and the lower section 130 or 220 of each of the first and second distillation columns 100 and 200. In the present specification, the upper section, the lower section and the intermediate section of the distillation column are relative concepts. The tops of the first and second distillation columns 100 and 200 are included in the upper sections, and the bottoms of the first and second distillation columns 100 and 200 are included in the lower sections thereof. Unless mentioned otherwise, "upper section" is synonymous with "the top of a column," and "lower section" is synonymous with "the bottom of a column." The first and second distillation columns 100 and 200 may be distillation columns with a theoretical plate number of 10 to 30, 12 to 28, or 15 to 25. The expression "theoretical plate number" means the number of hypothetical areas or plates, in which two phases such as a vapor phase and a liquid phase establish equilibrium with each other, of the first and second distillation columns 100 and 200.

In an embodiment, as illustrated in the FIGURE, the first distillation unit 10 includes the first distillation column 100 and the first condenser 101, the storage tank 102, and the first reboiler 103 connected to the first distillation column 100. The second distillation unit 20 includes the second distillation column 200 and the second condenser 201, the storage tank 202, and the second reboiler 203 connected to the second distillation column 200, as illustrated in FIG. the FIGURE. For example, the first distillation column 100, the first condenser 101, the storage tank 102, and the first reboiler 103 may be fluidically connected to each other such that fluid introduced into the first distillation column 100 flows thereinto. The second distillation column 200, the second condenser 201, the storage tank 202, and the second reboiler 203 may be fluidically connected to each other such that fluid introduced into the second distillation column 200 flows thereinto. In addition, the first distillation columns 100 and 200 may be fluidically connected to each other such that a bottom stream of the first distillation columns 100 is introduced into and flows in the intermediate section of the second distillation column 200. The condenser is separately installed on the outside of the distillation column and performs cooling using, for example, a method of bringing a stream discharged from the top of the distillation column into contact with cooling water introduced from the outside. For example, the first condenser 101 of the first distillation column 100 may condense the first top stream F1-2 discharged from the upper section 110 of the first distillation column 100, and the second condenser 201 of the second distillation column 200 may condense a second top stream F2-2 discharged through the upper section 210 of the second distillation column 200. In addition, the expression "reboiler" means a heating device separately installed on the outside of the distillation column. Alternatively, the reboiler may be a device for re-heating and evaporating a stream including ingredients with a high boiling point discharged through the bottom of the distillation column. For example, the first reboiler 103 of the first distillation column 100 may be a device for heating a column bottom stream F1-3 discharged through the lower section 130 of the first distillation column 100, and the second reboiler 203 of the second distillation column 200 to be described below may be a device for heating a column bottom stream F2-3 discharged through the lower section 230 of the second distillation column 200. "Storage tank" means a tank or a bath for temporarily storing a stream discharged from the distillation column and may be any tank or bath known in the art. For example, the first top stream F1-2 discharged from the upper section 110 of the first distillation column 100 is condensed in the first condenser 101, after which it is introduced into the storage tank 102 and stored therein. The second top stream F2-2 discharged from the upper section 210 of the second distillation column 200 may be condensed in the second condenser 201 and then introduced into the storage tank 202 and stored therein.

The first distillation column 100 includes a first supply port 121, and the second distillation column 200 includes a second supply port 221. In an embodiment, the first supply port 121 is located at an intermediate section 120 of the first distillation column 100, and the second supply port 221 is located at an intermediate section 220 of the second distillation column 200.

As illustrated in the FIGURE, a raw material F1-1 including compounds represented by Formulas 1 and 2 below and the isomer of the compound is introduced into the first supply port 121 of the first distillation column 100:

[Formula 1]

[Formula 2]

In Formula 1, $R_1$ is a $C_4$ to $C_{12}$ alkyl group, and $R_2$ to $R_4$ are each independently hydrogen or a $C_4$ to $C_{12}$ alkyl group.

In Formula 2, $R_5$ is a $C_1$ to $C_4$ alkyl group, and n is 1 to 4.

In an example, the compound represented by Formula 1 may be at least one selected from the group consisting of, for example, 1-octene, iso-octene, and a mixture thereof, and the compound represented by Formula 2 may be n-hexane, although the present application is not limited thereto.

In an example, as illustrated in the FIGURE, the raw material F1-1 introduced into the first supply port 121 of the first distillation column 100 is introduced into the intermediate section 120 of the first distillation column 100, and a raw material F1-1 introduced into the intermediate section 120 of the first distillation column 100 is separately discharged into each of a column top stream discharged through the upper section 110 of the first distillation column 100 and a column bottom stream discharged from the lower section 130 of the first distillation column 100. In this case, the column bottom stream discharged from the lower section 130 of the first distillation column 100 may be separately discharged into at least one stream. For example, the raw material F1-1 introduced into the first distillation column 100 may be separately discharged into each of the first top stream F1-2, and the first, second and third bottom streams F1-3, F1-4, and F1-5 discharged from the lower section 130 of the first distillation column 100.

The first top stream $F_{1-2}$ discharged from the upper section 110 of the first distillation column 100 is introduced into the first condenser 101, and a portion or all of the first top stream $F_{1-2}$ passing through the first condenser 101 may be refluxed into the upper section 110 of the first distillation column 100 or stored as a product. In an example, a stream discharged from the first condenser 101 may be introduced into the storage tank 102 and stored therein, and then refluxed into the first distillation column 100 or stored as a product. In addition, the first bottom stream $F_{1-3}$ discharged from the lower section 130 of the first distillation column 100 is introduced into the first reboiler 103. The first bottom stream $F_{1-3}$ passing through the first reboiler 103 may be introduced into the lower section 130 of the first distillation column 100. The first bottom stream $F_{1-3}$ introduced into the first reboiler 103 may be heated by high-pressure stream passing through the first reboiler 103. The amount of this high-pressure stream may be properly controlled by the heat exchanger 30 to be described below. For example, when heat exchange in the heat exchanger 30 is sufficiently carried out, the high-pressure stream may not be used at all. However, when heat exchange is not smoothly carried out due to a large discharge of a raw material or disturbance during a process, isolation efficiency may rapidly decrease. Accordingly, a proper amount of the high-pressure stream may be temporarily used so that robust isolation efficiency can be maintained despite disturbance.

The second bottom stream $F_{1-4}$ discharged from the lower section 130 of the first distillation column 100 is introduced into the second supply port 221 of the second distillation column 200. The second bottom stream $F_{1-4}$ introduced into the second supply port 221 of the second distillation column 200 is introduced into the intermediate section 220 of the second distillation column 200. The second bottom stream $F_{1-4}$ introduced into the intermediate section 220 of the second distillation column 200 is separately discharged into a column top stream discharged from the upper section 210 of the second distillation column 200 and a column bottom stream discharged from the lower section 230 of the second distillation column 200. In this case, the column bottom stream discharged from the lower section 230 of the second distillation column 200 may be separately discharged into at least one stream. For example, a stream introduced into the second distillation column 200 may be separately discharged into the second top stream $F_{2-2}$, and a fourth bottom stream $F_{2-3}$ and a fifth bottom stream $F_{2-4}$ discharged from the lower section 230 of the second distillation column 200.

The fourth bottom stream F2-3 discharged from the lower section 230 of the second distillation column 200 is introduced into the second reboiler 203. The fourth bottom stream F2-3 passing through the second reboiler 203 is introduced into the lower section 230 of the second distillation column 200, and the fifth bottom stream F2-4 discharged from the lower section 230 of the second distillation column 200 may be stored as a product in storage unit 204.

The heat exchanger 30 may be directly or indirectly connected to pipes through which the third bottom stream $F_{1-5}$ of the first distillation column 100 and the second top stream $F_{2-2}$ of the second distillation column 200 pass. In an example, the heat exchanger 30 is directly connected to the pipes through which the third bottom stream $F_{1-5}$ of the first distillation column 100 and the second top stream $F_{2-2}$ of the second distillation column 200 pass, whereby heat exchange between the third bottom stream $F_{1-5}$ and the second top stream $F_{2-2}$ may be efficiently performed.

Heat exchange between the third bottom stream $F_{1-5}$ and the second top stream $F_{2-2}$ introduced into the heat exchanger 30 is carried out, the third bottom stream $F_{1-5}$ passing through the heat exchanger 30 is refluxed into the lower section 130 of the first distillation column 100, the second top stream $F_{2-2}$ passing through the heat exchanger 30 is introduced into the second condenser 201, and a portion or all of the second top stream $F_{2-2}$ passing through the second condenser 201 may be refluxed into the upper section 210 of the second distillation column 200 or stored as a product. In an example, a stream discharged from the second condenser 201 is introduced in the storage tank 202 and stored therein. Subsequently, the stored stream may be refluxed into the second distillation column 200 or stored as a product.

In the heat exchanger 30, the third bottom stream $F_{1-5}$ may exchange heat with the second top stream $F_{2-2}$ before the third bottom stream $F_{1-5}$ is refluxed into the first distillation column 100, and the second top stream $F_{2-2}$ may exchange heat with the third bottom stream $F_{1-5}$ before the second top stream $F_{2-2}$ is introduced into the second condenser 201. For example, the second top stream $F_{2-2}$ including an ingredient with a low boiling point discharged from the upper section 210 of the second distillation column 200 transits the heat exchanger 30 before being refluxed into the upper section 210 of the second distillation column 200. At this time, heat is supplied to the heat exchanger 30. Accordingly, the second top stream $F_{2-2}$ discharged from the second distillation column 200 may be refluxed at a relatively low temperature in the second distillation column 200. Accordingly, the quantity of heat necessary to condense the second top stream $F_{2-2}$ discharged from the upper section 210 of the second distillation column 200 may be decreased, and costs necessary for the condensation process may be reduced by decreasing the amount of cooling water used in the condensation process in which the second condenser 201 is used. In addition, the third bottom stream $F_{1-5}$, is a stream including an ingredient with a high boiling point discharged from the lower section 130 of the first distillation column 100, and transits the heat exchanger 30 before being refluxed into the lower section 130 of the first distillation column 100. At this time, heat transferred by the second top stream $F_{2-2}$ may be supplied to the third bottom stream $F_{1-5}$. Accordingly, the second top stream $F_{2-2}$ supplies heat to the lower section 130 of the first distillation column 100 and thus the amount of the stream used in the first reboiler 103 in order to heat the first bottom stream $F_{1-3}$ discharged from the lower section 130 of the first distillation column 100 is reduced, thereby reducing costs.

Hereinafter, a process of isolating an olefin monomer, a solvent, and a raw material such as, for example, 1-octene/iso-octene, n-hexane, etc. used in polymerizing the polyolefin elastomer by means of the distillation device according to an embodiment of the present application will be described in detail.

In an example, the raw material $F_{1-1}$ including 1-octene or iso-octene represented by Formula 1 or a mixture thereof, and n-hexane represented by Formula 2 as main ingredients is introduced into the first supply port 121 of the first distillation column 100.

In this case, a stream including a large amount of n-hexane with a relatively low boiling point among ingredients that are included in the raw material $F_{1-1}$ introduced into the first supply port 121 may be discharged as the first top stream $F_{1-2}$ from the upper section 110 of the first distillation column 100, and a stream including a large amount of 1-octene or iso-octene with a relatively high boiling point may be discharged as the first top stream $F_{1-2}$, and the first, second and third bottom streams $F_{1-3}$, $F_{1-4}$, and $F_{1-5}$ from the lower section 130 of the first distillation column 100. The first top stream $F_{1-2}$ discharged through the upper section 110 of the first distillation column 100 is introduced into the storage tank 102 via the first condenser 101. A portion of the stream discharged from the storage tank 102 is refluxed into the upper section 110 of the first distillation column 100, and a portion of the remainder of the stream may be stored as a product. The product may be high-purity n-hexane. Meanwhile, the first bottom stream $F_{1-3}$ discharged from the lower section 130 of the first distillation column 100 may be refluxed into the lower section 130 of the first distillation column 100 via the first reboiler 103, and the second bottom stream $F_{1-4}$ may be introduced into the second supply port 221 of the second distillation column 200. In addition, the third bottom stream $F_{1-5}$ may exchange heat with the second top stream $F_{2-2}$ of the second distillation column 200 in the heat exchanger 30, and then be refluxed into the lower section 130 of the first distillation column 100.

In addition, the second bottom stream $F_{1-4}$ introduced into the second supply port 221 includes 1-octene and/or iso-octene and ingredients with a high boiling point. Accordingly, a stream including a large amount of 1-octene and/or iso-octene with a relatively low boiling point among ingredients included the second bottom stream $F_{1-4}$ may be discharged as the second top stream $F_{2-2}$ from the upper section 210 of the second distillation column 200, and a stream including ingredients with a relatively high boiling point may be discharged as the fourth and fifth bottom streams $F_{2-3}$ and $F_{2-4}$ from the lower section 230 of the second distillation column 200. The discharged second top stream $F_{2-2}$ exchanges heat with the third bottom stream $F_{1-5}$ of the first distillation column 100 in the heat exchanger 30 and is then introduced into the storage tank 202 via the second condenser 201. A portion of the stream discharged from the storage tank 202 may be refluxed into the upper section 210 of the second distillation column 200, and another portion of the stream may be stored as a product. The product may be high-purity 1-octene and/or iso-octene. In addition, a stream including an ingredient with a relatively high boiling point among ingredients included in the second top stream $F_{2-2}$ may be discharged as the fourth and fifth bottom streams $F_{2-3}$ and $F_{2-4}$ from the lower section 230 of the second distillation column 200. The fourth bottom stream $F_{2-3}$ may be refluxed into the lower section 230 of the second distillation column 200 via the second reboiler 203 and the fifth bottom stream $F_{2-4}$ may be utilized as fuel. The fifth bottom stream $F_{2-4}$ may be, for example, an octene-based ingredient and/or an ingredient with a high boiling point.

In the present specification, the expression "stream including an ingredient with a low boiling point" means a stream including a large amount of an ingredient with a relatively low boiling point of the raw material stream $F_{1-1}$ including an ingredient with a low boiling point and an ingredient with a high boiling point. For example, streams including ingredients with low boiling points are streams discharged from the upper sections 110 and 210 of the first and second distillation columns 100 and 200. In addition, the expression "stream including an ingredient with a high boiling point" means a stream including a large amount of an ingredient with a relatively high boiling point of the raw material stream $F_{1-1}$ including an ingredient with a low boiling point and an ingredient with a high boiling point. For example, a stream including an ingredient with a high boiling point is a stream including a large amount of an ingredient with a relatively high boiling point discharged from the lower sections 130 and 230 of the first and second distillation columns 100 and 200. The expression "stream including a large amount of an ingredient" means a stream in which the content of each of an ingredient with a low boiling point included in a stream discharged from the upper sections 110 and 210 of the first and second distillation columns 100 and 200 and an ingredient with a high boiling point included in a stream discharged from the lower sections 130 and 230 of the first and second distillation columns 100 and 200 is higher than the content of each of the ingredient with a low boiling point and the ingredient with a high boiling point included in the raw material $F_{1-1}$. For example, the content of each of the ingredient with a low boiling point included in the first top stream $F_{1-2}$ of the first distillation column 100 and the ingredient with a low boiling point included in the second top stream $F_{2-2}$ of the second distillation column 200 may be 50% by weight or more, 80% by weight or more, 90% by weight or more, 95% by weight or more or 99% by weight or more. Alternatively, the contents of an ingredient with a high boiling point included in each of the first top stream $F_{1-2}$, and the first, second and third bottom streams $F_{1-3}$, $F_{1-4}$, and $F_{1-5}$ of the first distillation column 100 and an ingredient with a high boiling point included in each of the fourth and fifth bottom streams $F_{2-3}$ and $F_{2-4}$ of the second distillation column 200 may each be 50% by weight or more, 80% by weight or more, 90% by weight or more, 95% by weight or more, or 99% by weight or more.

In an example, a portion of the fifth bottom stream $F_{2-4}$ discharged from the lower section 230 of the second distillation column 200 may be introduced into the lower section 130 of the first distillation column 100, for example, a 13th to 23rd plate of the first distillation column 100 with a theoretical plate number of 15 to 25. Accordingly, 1-octene and/or iso-octene that may remain in the fifth bottom stream $F_{2-4}$ may be supplied to the lower section 130 of the first distillation column 100, and thereby 1-octene and/or iso-octene with higher purity may be prepared. In this case, a ratio of the discharge rate (kg/hr) of the stream introduced into the lower section 130 of the first distillation column 100 to a discharge rate (kg/hr) of the fifth bottom stream $F_{2-4}$ discharged from the lower section 230 of the second distillation column 200 may be 1:0.8 to 1:0.95. By controlling a discharge ratio of the stream introduced into the lower section 130 of the first distillation column 100 within this range, 1-octene and/or iso-octene with higher purity may be prepared.

In an embodiment, the distillation device of the present application satisfies Equation 1 below.

$$T_{t-2} - T_{b-3} \geq 8° \text{C}. \qquad \text{[Equation 1]}$$

wherein $T_{t-2}$ indicates the temperature of the second top stream $F_{2-2}$, and $T_{b-3}$ indicates the temperature of the third bottom stream $F_{1-5}$.

When the distillation device of the present application satisfies Equation 1, the compounds represented by Formulas 1 and 2, particularly 1-octene/iso-octene and n-hexane, may be isolated with superior efficiency and high purity using the distillation device with the aforementioned series structure. That is, by controlling the distillation device such that a temperature difference between the second top stream $F_{2-2}$ and the third bottom stream $F_{1-5}$ satisfies Equation 1, heat exchange efficiency between the second top stream $F_{2-2}$ and the third bottom stream $F_{1-5}$ may be maximized. Accordingly, the compounds represented by Formulas 1 and 2, particularly 1-octene, iso-octene, or a mixture thereof and n-hexane, may be isolated with superior efficiency and high purity.

In an example, as long as a temperature difference between the second top stream $F_{2-2}$ discharged from the upper section 210 of the second distillation column 200 and the third bottom stream $F_{1-5}$ discharged from the lower section 130 of the first distillation column 100 satisfies Equation 1, there is no specific limitation. For example, the temperature difference may be 8° C. or more, 9° C. or more, 10° C. or more, 13° C. or more, or 15° C. or more. Since heat exchange efficiency is superior when the temperature difference between the second top stream $F_{2-2}$ discharged from the upper section 210 of the second distillation column 200 and the third bottom stream $F_{1-5}$ discharged from the lower section 130 of the first distillation column 100 increases, the maximum value of the temperature difference value is not specifically limited. For example, a temperature difference between the second top stream $F_{2-2}$ discharged from the upper section 210 of the second distillation column 200 and the third bottom stream $F_{1-5}$ discharged from the lower section 130 of the first distillation column 100 may be 100° C. or less, considering process efficiency.

In an example, the distillation device of the present application satisfies Equation 2 below:

$$P_2/P_1 \geq 3.0 \quad \text{[Equation 2]}$$

wherein $P_1$ indicates the pressure (kg/cm² g) of the upper section 110 of the first distillation column 100, and $P_2$ indicates the pressure (kg/cm² g) of the upper section 210 of the second distillation column 200.

When the distillation device of the present application satisfies Equation 1, 1-octene or iso-octene represented by Formula 1 or a mixture thereof and n-hexane represented by Formula 1 may be isolated in superior efficiency and high purity using the distillation device with the aforementioned series structure. That is, by controlling the distillation device such that a ratio of the pressure of the upper section 210 of the second distillation column 200 to the pressure of the upper section 110 of the first distillation column 100 satisfies Equation 2, heat exchange efficiency between the second top stream $F_{2-2}$ and the third bottom stream $F_{1-5}$ may be maximized. Accordingly, 1-octene or iso-octene represented by Formula 1 or a mixture thereof and n-hexane represented by Formula 2 may be isolated with superior efficiency and high purity.

For example, in order to increase the heat exchange efficiency of the heat exchanger 30, the interior temperature of the first distillation column 100 may be kept lower than the interior temperature of the second distillation column 200, and thus the pressure of the upper section 110 of the first distillation column 100 may be kept lower than that of the upper section 210 of the second distillation column 200.

In an example, as long as a ratio of the pressure of the upper section 210 of the second distillation column 200 to the pressure of the upper section 110 of the first distillation column 100 satisfies Equation 2, there is no specific limitation. For example, the ratio may be 3.0 or more, 4.0 or more, 5.0 or more, or 8.0 or more. Since heat exchange efficiency improves when the ratio of the pressure of the upper section 210 of the second distillation column 200 to the pressure of the upper section 110 of the first distillation column 100 increases, the maximum value of the ratio is not specifically limited. For example, the ratio of the pressure of the upper section 210 of the second distillation column 200 to the pressure of the upper section 110 of the first distillation column 100 may be 200 or less, or 100 or less, considering process efficiency.

The temperature of the second top stream $F_{2-2}$ discharged from the upper section 210 of the second distillation column 200 is not specifically limited as long as Equation 1 is satisfied. The temperature may be 125 to 170° C., for example, 130° C. to 168° C. or 140° C. to 165° C. In addition, the temperature of the third bottom stream $F_{1-5}$ discharged from the lower section 130 of the first distillation column 100 is not specifically limited as long as Equation 1 is satisfied. The temperature may be 120° C. to 145° C., for example, 122° C. to 140° C. or 125° C. to 135° C. In this case, the pressure of the upper section 110 of the first distillation column 100 is not specifically limited as long as Equation 2 is satisfied. The pressure may be 0.05 to 0.2 kg/cm² g, 0.08 to 0.18 kg/cm² g, or 0.1 to 0.16 kg/cm² g. In addition, the pressure of the upper section 210 of the second distillation column 200 is not specifically limited as long as Equation 2 is satisfied. The pressure may be 1.0 to 2.0 kg/cm² g, 1.1 to 1.8 kg/cm² g, or 1.2 to 1.6 kg/cm² g.

In an example, the temperature of the upper section 110 of the first distillation column 100 may be 60° C. to 80° C., for example, 62° C. to 78° C. or 64° C. to 76° C., and the temperature of the lower section 130 of the first distillation column 100 may be 120° C. to 145° C., for example, 122° C. to 140° C. or 124° C. to 135° C., although the present application is not limited thereto. In this case, the temperature of the upper section 210 of the second distillation column 200 may be 125° C. to 170° C., for example, 130° C. to 168° C. or 140° C. to 165° C., and the temperature of the lower section 230 of the second distillation column 200 may be 130° C. to 180° C., for example, 135° C. to 175° C. or 140° C. to 170° C., although the present application is not limited thereto.

The present disclosure also relates to a distillation method of isolating the solvent used in the polyolefin elastomer polymerization process from the unreacted olefin monomer.

The distillation method according to an exemplary embodiment of the present application may be carried out using the aforementioned distillation device, and thus the same content as the description of the aforementioned distillation device is omitted.

In an embodiment, the distillation method of the present application includes a) a step of introducing the raw material $F_{1-1}$ including the compounds represented by Formulas 1 and 2 below into the first supply port 121 of the first distillation column 100; b) a step of discharging the introduced raw material $F_{1-1}$ to each of the first top stream $F_{1-2}$ discharged from the upper section 110 of the first distillation column 100; and the first top stream $F_{1-2}$, and the first, second and third bottom streams $F_{1-3}$, $F_{1-4}$, and $F_{1-5}$ discharged from the lower section 130 of the first distillation column 100; c) a step of introducing the first bottom stream $F_{1-3}$ into the second supply port 221 of the second distillation column 200; d) a step of discharging the stream introduced into the second supply port 221 to each of the second top stream $F_{2-2}$ discharged from the upper section 210 of the second distillation column 200, and the fourth and fifth bottom streams $F_{2-3}$ and $F_{2-4}$ discharged from the lower section 230 of the second distillation column 200; e) a step of exchanging heat between the second top stream $F_{2-2}$ and the third bottom stream $F_{1-5}$; and f) a step of isolating the compound represented by Formula 2 from the upper section 110 of the first distillation column 100, and the compound represented by Formula 1 from the upper section 210 of the second distillation column 200:

[Formula 1]

[Formula 2]

In Formula 1, $R_1$ is a $C_4$ to $C_{12}$ alkyl group, and $R_2$ to $R_4$ are each independently hydrogen or a $C_4$ to $C_{12}$ alkyl group.

In Formula 2, $R_5$ is a $C_1$ to $C_4$ alkyl group, and n is 1 to 4.

The distillation method may be carried out using the aforementioned distillation device. Description of the distillation device is the same as that given above, and is thus omitted.

As described above, steps a) to f) are each independently organically connected, and thus boundaries therebetween are not clearly divided according to chronological order. Each of steps a) to f) may be carried out sequentially or independently at the same time.

The distillation method satisfies Equations 1 and 2 below. Description thereof is the same as that given above, and is thus omitted.

$$T_{t-2} - T_{b-3} \geq 8° C. \quad \text{[Equation 1]}$$

$$P_2/P_1 \geq 3.0 \quad \text{[Equation 2]}$$

In Equation 1, $T_{t-2}$ indicates the temperature of the second top stream $F_{2-2}$, and $T_{b-3}$ indicates the temperature of the third bottom stream $F_{1-5}$.

In Equation 2, $P_1$ indicates the pressure (kg/cm$^2$ g) of the upper section 110 of the first distillation column 100, and $P_2$ indicates the pressure (kg/cm$^2$ g) of the upper section 210 of the second distillation column 200.

Advantageous Effects

As apparent from the foregoing, the distillation device of the present application can minimize energy loss occurring in a purification process of the olefin monomer, the solvent, and the raw material including, for example, 1-octene/iso-octene and n-hexane, used in a polymerization process of the polyolefin elastomer, and can increase economic efficiency by isolating a high-purity product.

DESCRIPTION OF DRAWINGS

The FIGURE exemplarily illustrates a distillation device according to an embodiment of the present application.

MODES OF THE INVENTION

Figure 1:
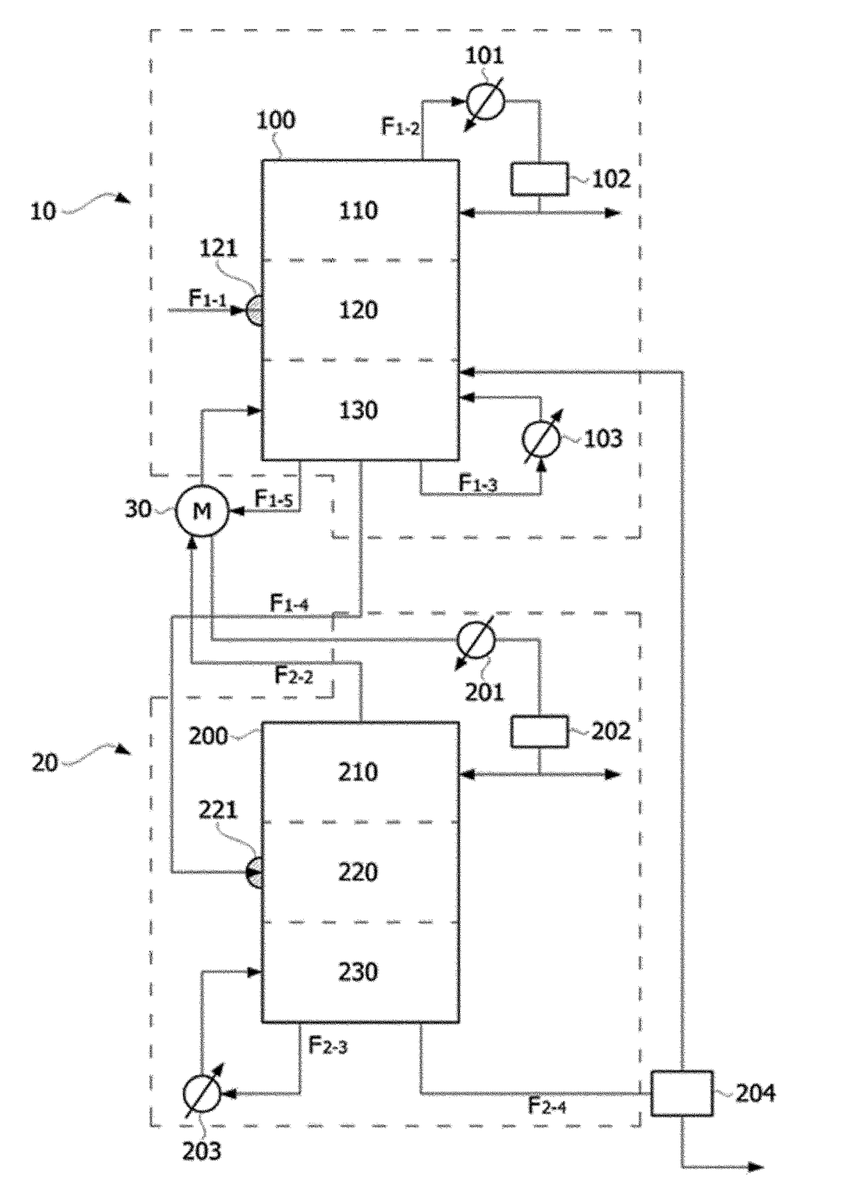

Now, the present invention will be described in more detail with reference to examples according to the present invention and comparative examples. These examples are provided for illustrative purposes only and should not be construed as limiting the scope and spirit of the present invention.

Example 1

1-Octene, iso-octene, and n-hexane were isolated by means of a distillation device illustrated in the FIGURE. In particular, a raw material including 1-octene, iso-octene, and n-hexane was introduced into a first supply port located at a 15th plate of a first distillation column with a theoretical plate number of 21.

A portion of a first top stream discharged from an upper section of the first distillation column was refluxed into the upper section of the first distillation column via a first condenser. A portion of the remainder of the first top stream was isolated as a product including n-hexane and stored. A portion of a first bottom stream discharged from a lower section of the first distillation column was refluxed into the lower section of the first distillation column via a first reboiler. A second bottom stream discharged from the lower section of the first distillation column was introduced into a second supply port located at a 7$^{th}$ plate of a second distillation column with a theoretical plate number of 12. A third bottom stream discharged from the lower section of the first distillation column was introduced into a heat exchanger and heat-exchanged with a second top stream of the second distillation column introduced into the heat exchanger, and then was refluxed into the lower section of the first distillation column via the heat exchanger. In this case, operation pressure of the upper section of the first distillation column was adjusted to 0.16 kg/cm$^2$ g and an operation temperature thereof was adjusted to 75° C. An operation temperature of the lower section of the first distillation column was adjusted to 130° C.

Meanwhile, the second top stream discharged from an upper section of the second distillation column was introduced into the heat exchanger and heat-exchanged with the third bottom stream. Subsequently, a portion of the second top stream having passed through the heat exchanger and the second condenser was refluxed into the upper section of the second distillation column, and a portion of the remainder of the second top stream was isolated as an octene-based product including 1-octene and iso-octene. In this case, the purity of each of the 1-octene and iso-octene was 94%. A fourth bottom stream discharged from a lower section of the second distillation column was refluxed into the lower section of the second distillation column via a second reboiler, and a fifth bottom stream discharged from the lower section of the second distillation column was isolated as a product for fuel including some octene-based materials and an ingredient with a high boiling point. In this case, operation pressure of the upper section of the second distillation column was adjusted to 1.4 kg/cm$^2$ g, and an operation temperature thereof was adjusted to 155° C. An operation temperature of the lower section of the second distillation column was adjusted to 160° C.

In isolating 1-octene, iso-octene, and n-hexane by means of the distillation device of Example 1, a used energy amount, a recovery amount, a reduction amount, a reduction rate, and the purities of a mixture of 1-octene and iso-octene, and an n-hexane product were as summarized in Table 1 below.

Example 2

1-Octene, iso-octene, and n-hexane were isolated in the same manner as in Example 1, except that the operation conditions of the first and second distillation columns were changed as disclosed in Table 1 below.

In isolating 1-octene, iso-octene, and n-hexane by means of a distillation device of Example 2, a used energy amount, a recovery amount, a reduction amount, a reduction rate, and the purities of a mixture of 1-octene and iso-octene, and an n-hexane product were as summarized in Table 1 below.

Example 3

1-Octene, iso-octene, and n-hexane were isolated in the same manner as in Example 1, except that the operation conditions of the first and second distillation columns were changed as disclosed in Table 1 below.

In isolating 1-octene, iso-octene, and n-hexane by means of a distillation device of Example 3, a used energy amount, a recovery amount, a reduction amount, a reduction rate, and the purities of a mixture of 1-octene and iso-octene, and an n-hexane product were as summarized in Table 1 below.

Example 4

1-Octene, iso-octene, and n-hexane were isolated in the same manner as in Example 1, except that the operation conditions of the first and second distillation columns were changed as disclosed in Table 1 below.

In isolating 1-octene, iso-octene, and n-hexane by means of a distillation device of Example 4, a used energy amount, a recovery amount, a reduction amount, a reduction rate, and the purities of a mixture of 1-octene and iso-octene, and an n-hexane product were as summarized in Table 1 below.

Comparative Example 1

1-Octene, iso-octene, and n-hexane were isolated in the same manner as in Example 1, except that the operation conditions of the first and second distillation columns were changed as disclosed in Table 2 below.

In isolating 1-octene, iso-octene, and n-hexane by means of a distillation device of Comparative Example 1, a used energy amount, a recovery amount, a reduction amount, a reduction rate, and the purities of a mixture of 1-octene and iso-octene, and an n-hexane product were as summarized in Table 2 below.

Comparative Example 2

1-Octene, iso-octene, and n-hexane were isolated in the same manner as in Example 1, except that the operation conditions of the first and second distillation columns were changed as disclosed in Table 2 below.

In isolating 1-octene, iso-octene, and n-hexane by means of a distillation device of Comparative Example 2, a used energy amount, a recovery amount, a reduction amount, a reduction rate, and the purities of a mixture of 1-octene and iso-octene, and n-hexane were as summarized in Table 2 below.

Comparative Example 3

1-Octene, iso-octene, and n-hexane were isolated in the same manner as in Example 1, except that the operation conditions of the first and second distillation columns were changed as disclosed in Table 2 below.

In isolating 1-octene, iso-octene, and n-hexane by means of a distillation device of Comparative Example 3, a used energy amount, a recovery amount, a reduction amount, a reduction rate, and the purities of a mixture of 1-octene and iso-octene, and an n-hexane product were as summarized in Table 2 below.

Comparative Example 4

1-Octene, iso-octene, and n-hexane were isolated in the same manner as in Example 1, except that the operation conditions of the first and second distillation columns were changed as disclosed in Table 3 below.

In isolating 1-octene, iso-octene, and n-hexane by means of a distillation device of Comparative Example 4, a used energy amount, a recovery amount, a reduction amount, a reduction rate, and the purities of a mixture of 1-octene and iso-octene, and an n-hexane product were as summarized in Table 3 below.

Comparative Example 5

1-Octene, iso-octene, and n-hexane were isolated in the same manner as in Example 1, except that the operation conditions of the first and second distillation columns were changed as disclosed in Table 3 below.

In isolating 1-octene, iso-octene, and n-hexane by means of a distillation device of Comparative Example 5, a used energy amount, a recovery amount, a reduction amount, a reduction rate, and the purities of a mixture of 1-octene and iso-octene, and an n-hexane product were as summarized in Table 3 below.

TABLE 1

| | | Example 1 | Example 2 | Example 3 | Example 4 |
|---|---|---|---|---|---|
| Pressure of upper section (kg/cm$^2$g) | First distillation column | 0.16 | 0.13 | 0.15 | 0.05 |
| | Second distillation column | 1.4 | 1.1 | 1.2 | 1.2 |
| Column temperature (° C.) (upper section/lower section) | First distillation column | 75/130 | 72/126 | 74/130 | 71/127 |
| | Second distillation column | 155/160 | 149/155 | 151/157 | 151/157 |
| Energy (Gcal/hr) | First distillation column | 0.7 | 0.83 | 0.88 | 0.74 |
| | Second distillation column | 0.73 | 0.74 | 0.74 | 0.74 |
| | Recovery amount | 0.7 | 0.63 | 0.62 | 0.67 |
| | Total | 0.73 | 0.94 | 1.00 | 0.81 |
| | Reduction amount | 0.59 | 0.38 | 0.32 | 0.51 |
| | Energy reduction rate (%) | 44.7 | 28.8 | 24.2 | 38.6 |
| Product purity (%) | 1-Octene + iso-octene | 94 | 94 | 94 | 94 |
| | n-Hexane | 99.3 | 99.3 | 99.3 | 99.3 |

TABLE 2

|  |  | Comparative Example 1 | Comparative Example 2 | Comparative Example 3 |
|---|---|---|---|---|
| Pressure of upper section ($kg/cm^2g$) | First distillation column | 0.3 | 0.75 | 0.75 |
|  | Second distillation column | 0.2 | 1.2 | 2.0 |
| Column temperature (° C.) (upper section/lower section) | First distillation column | 80/135 | 88/144 | 88/144 |
|  | Second distillation column | 130/135 | 151/157 | 166/172 |
| Energy (Gcal/hr) | First distillation column | 0.73 | 1.73 | 1.73 |
|  | Second distillation column | 0.59 | 0.74 | 0.96 |
|  | Recovery amount | — | 0.45 | 0.45 |
|  | Total | 1.32 | 2.02 | 2.24 |
|  | Reduction amount | — | — | — |
|  | Energy reduction rate (%) | — | — | — |
| Product purity (%) | 1-Octene + iso-octene | 94 | 94 | 94 |
|  | n-Hexane | 99.3 | 99.3 | 99.3 |

TABLE 3

|  |  | Comparative Example 4 | Comparative Example 5 |
|---|---|---|---|
| Pressure of upper section ($kg/cm^2g$) | First distillation column | 0.75 | 0.68 |
|  | Second distillation column | 1.23 | 1.15 |
| Column temperature (° C.) (upper section/lower section) | First distillation column | 88/144 | 86/143 |
|  | Second distillation column | 152/160 | 151/159 |
| Energy (Gcal/hr) | First distillation column | 1.73 | 1.58 |
|  | Second distillation column | 0.77 | 0.70 |
|  | Recovery amount | 0.45 | 0.45 |
|  | Total | 2.05 | 1.83 |
|  | Reduction amount | — | — |
|  | Energy reduction rate (%) | — | — |
| Product purity (%) | 1-Octene + iso-octene | 94 | 94 |
|  | n-Hexane | 99.3 | 99.3 |

As shown in Tables 1 to 3, it can be confirmed that, when 1-octene, iso-octene, and n-hexane are isolated according to each of Examples 1 to 4, a total energy consumption amount is greatly decreased, compared to the comparative examples. Accordingly, when the raw material is isolated by means of the distillation device according to each of Examples 1 to 4 of the present application, energy reduction effect up to 44.7% can be achieved, compared to the cases in which the distillation devices according to the comparative examples are used.

In addition, it can be confirmed that, as shown in the examples and the comparative examples, 1-octene, iso-octene, and n-hexane can be isolated with high purity and efficiency by controlling a temperature difference between the lower section of the first distillation column and the upper section of the second distillation column and the pressures of the upper sections of the first and second distillation columns within a specific range.

The invention claimed is:
1. A distillation method, comprising:
introducing a raw material comprising compounds represented by Formulas 1 and 2 below into a first supply port of a first distillation column,
obtaining a first top stream at an upper section of the first distillation column, and separately obtaining first, second and third bottom streams at a bottom section of the first distillation column,
introducing the first bottom stream into a second supply port of a second distillation column,
obtaining a second top stream at an upper section of a second distillation column and obtaining fourth and fifth bottom streams at a bottom section of the second distillation column,
heat-exchanging the second top stream with the third bottom stream; and
isolating the compound represented by Formula 2 from the first top stream, and the compound represented by Formula 1 from the second top stream,
wherein Equations 1 and 2 below are satisfied:

[Formula 1]

[Formula 2]

wherein $R_1$ is a $C_4$ to $C_{12}$ alkyl group, and $R_2$ to $R_4$ are each independently hydrogen or a $C_4$ to $C_{12}$ alkyl group,
$R_5$ is a $C_1$ to $C_4$ alkyl group, and n is 1 to 4;

$$T_{t-2} - T_{b-3} \geq 8° C., \quad \text{[Equation 1]}$$

$$P_2/P_1 \geq 3.0, \quad \text{[Equation 2]}$$

wherein $T_{t-2}$ indicates a temperature of the second top stream, and $T_{b-3}$ indicates a temperature of the third bottom stream, and
$P_1$ indicates a pressure of the upper section of the first distillation column in $kg/cm^2$ g, and $P_2$ indicates a pressure of the upper section of the second distillation column in $kg/cm^2$ g.

2. The method according to claim 1, wherein the compound represented by Formula 1 is at least one selected from the group consisting of 1-octene, iso-octene and a mixture thereof, and the compound represented by Formula 2 is n-hexane.

3. The method according to claim 2, wherein a content of n-hexane in the first top stream is 90% or more, and a content of 1-octene, iso-octene, or a mixture thereof in the second top stream is 90% or more.

4. The method according to claim 1, wherein the second top stream that is heat-exchanged with the third bottom stream is introduced into a second condenser, which is in fluid communication with the second distillation column, and a portion of the second top stream passing through the second condenser is introduced into the upper section of the second distillation column, and a remainder of the second top stream passing through the second condenser is introduced into a storage tank to store the compound represented by Formula 1 therein.

5. The method according to claim 1, wherein a pressure of the upper section of the first distillation column is 0.05 to 0.2 kg/cm² g.

6. The method according to claim 1, wherein a pressure of the upper section of the second distillation column is 1.0 to 2.0 kg/cm² g.

7. The method according to claim 1, wherein a temperature of the upper section of the first distillation column is 60 to 80° C.

8. The method according to claim 1, wherein a temperature of the lower section of the first distillation column is 120 to 145° C.

9. The method according to claim 1, wherein a temperature of the upper section of the second distillation column is 125 to 170° C.

10. The method according to claim 1, wherein a temperature of the lower section of the second distillation column is 130 to 180° C.

11. The method according to claim 1, wherein the compound represented by Formula 2 is a solvent used in polymerization of a polyolefin elastomer.

* * * * *